(12) United States Patent
Verstraeten et al.

(10) Patent No.: US 9,008,386 B2
(45) Date of Patent: Apr. 14, 2015

(54) METHOD, A GRAPHIC USER INTERFACE, A SYSTEM AND A COMPUTER PROGRAM FOR OPTIMIZING WORKFLOW OF A MEDICAL INTERVENTION

(75) Inventors: Luc Verstraeten, Onze-Lieve-Vrouw-Waver (BE); Jan Svarovsky, London (GB); Gerard Burgstede, Veenendaal (NL); Frank Wessels, Bilthoven (NL)

(73) Assignee: 3mensio Medical Imaging B.V., Bilthoven (NL)

( * ) Notice: Subject to any disclaimer, the term of this patent is extended or adjusted under 35 U.S.C. 154(b) by 158 days.

(21) Appl. No.: 13/501,466

(22) PCT Filed: Oct. 14, 2009

(86) PCT No.: PCT/NL2009/050621
§ 371 (c)(1),
(2), (4) Date: Apr. 12, 2012

(87) PCT Pub. No.: WO2011/046425
PCT Pub. Date: Apr. 21, 2011

(65) Prior Publication Data
US 2012/0207365 A1    Aug. 16, 2012

(51) Int. Cl.
*G06K 9/00* (2006.01)
*G06T 19/00* (2011.01)
*G06T 7/00* (2006.01)
*G06F 19/00* (2011.01)

(52) U.S. Cl.
CPC ............... *G06T 19/00* (2013.01); *G06F 19/321* (2013.01); *G06F 19/3437* (2013.01); *G06T 7/0012* (2013.01); *G06T 2200/24* (2013.01); *G06T 2207/10072* (2013.01); *G06T 2207/30048* (2013.01); *G06T 2207/30101* (2013.01); *Y10S 128/922* (2013.01); *Y10S 128/923* (2013.01)

(58) Field of Classification Search
USPC .................... 382/128, 130, 131; 128/922, 923
See application file for complete search history.

(56) References Cited

U.S. PATENT DOCUMENTS

| | | | | |
|---|---|---|---|---|
| 6,969,355 | B2 * | 11/2005 | Narimatsu | 600/481 |
| 7,431,692 | B2 * | 10/2008 | Zollinger et al. | 600/37 |
| 7,871,368 | B2 * | 1/2011 | Zollinger et al. | 600/37 |
| 8,109,995 | B2 * | 2/2012 | Paniagua et al. | 623/2.14 |
| 8,177,835 | B2 * | 5/2012 | Noettling et al. | 623/2.1 |
| 8,241,274 | B2 * | 8/2012 | Keogh et al. | 606/32 |
| 8,449,466 | B2 * | 5/2013 | Duhay et al. | 600/439 |

(Continued)

OTHER PUBLICATIONS

"A Planning System for Transapical Aortic Valve Implantation", Gessat M et al, Proceedings of the SPIE on Medical Imaging 2009: Visualization, Image-Guided Procedures, and Modeling, vol. 7261, 72611E, Feb. 8, 2009, pp. 1-12 XP055001622, The International Society for Optical Engineering SPIE USA ISSN: 0277-786X section 2.

(Continued)

*Primary Examiner* — Yosef Kassa
(74) *Attorney, Agent, or Firm* — Gordon & Jacobson, PC (57) ABSTRACT

The invention relates to a method of optimizing workflow for an intervention, comprising the steps of reconstruction of an image of a target area representative of an envisaged intervention based on imaging dataset; automatically selecting an optimal viewing direction for enabling a pre-operative quantitative analysis of intervention features. The invention further relates to a computer program and a system for optimizing a workflow of an intervention.

23 Claims, 6 Drawing Sheets

(56) References Cited

U.S. PATENT DOCUMENTS

| | | | |
|---|---|---|---|
| 8,518,073 B2* | 8/2013 | Lashinski | 606/200 |
| 8,577,441 B2* | 11/2013 | Lorenz et al. | 600/410 |
| 2005/0113664 A1 | 5/2005 | Stefani et al. | |
| 2008/0009746 A1 | 1/2008 | Forster et al. | |

OTHER PUBLICATIONS

A New Automatic Mode of Visualizing the Colon Via Cine CT:, UDUPA et al. Proceedings of the SPIE—The International Society for Optical Engineering SPIE-INT. Soc. Opt. Eng. USA, vol. 4319, 2001, pp. 237-243, XP008138717, ISSN: 0277-786X abstract; section 2.

* cited by examiner

METHOD, A GRAPHIC USER INTERFACE, A SYSTEM AND A COMPUTER PROGRAM FOR OPTIMIZING WORKFLOW OF A MEDICAL INTERVENTION

CROSS-REFERENCE TO RELATED APPLICATIONS

This application claims priority from PCT/NL2009/050621 filed on Oct. 14, 2009, which is hereby incorporated by reference in its entirety.

BACKGROUND OF THE INVENTION

1. Field of the Invention

The invention relates to the field of medical interventions, in particular to the field of heart valve replacements or stent placements. More in particular the invention relates to a method of optimizing workflow for a medical intervention. The invention further relates to a computer program for optimizing workflow for an intervention. The invention still further relates to a graphic user interface for enabling optimization of the workflow for an intervention. The invention still further relates to a system for optimizing workflow for an intervention.

2. State of the Art

Medical interventions, in particular, cardiac and vascular interventions are gaining profound importance in contemporary medical practice. For example, annually a great number of interventions is carried out with respect to heart valve replacements.

It will be appreciated that the heart of a mammal, such as a human being or an animal, includes four valves (i.e. mitral valve, aortic valve, pulmonary valve and tricuspid valve). The mitral valve controls the blood flow between the left atrium and the left ventricle. The tricuspid valve controls the blood flow between the right atrium and the right ventricle. The aortic valve controls the blood flow from the left ventricle to the vascular system of the body. The pulmonary valve controls the blood flow from the right ventricle to the lungs. Defective operation of any of these four valves may cause a specific medical condition. For example, a defective mitral valve may cause regurgitation (i.e. leakage between the left ventricle and the left atrium), thereby reducing the pumping efficiency of the heart, and depriving major organs of the body from oxygen and the necessary substances.

During a medical intervention regarding a heart valve replacement a suitable heart valve is replaced by an artificial valve, which may be either a mechanical valve or a tissue valve. Those skilled in the art will readily appreciate which valves are commonly used for facilitating the heart valve replacement.

Regarding the course of intervention, a closed-chest setting is preferred wherein access to the heart valve is gained either by performing a number of access holes in the chest or by entering the heart chambers through the vascular system, for example through the right subclavian vein, or inferior vena cava. Such closed-chest approach is commonly referred to as a minimally invasive surgery, which has gained its acknowledgement due to a considerable reduction of complications with respect to complications occurring after an open-chest surgery.

It is appreciated that for a successful intervention, be it a heart valve replacement or placing of a stent, accurate knowledge about target anatomy and position is required.

An embodiment of a method of assessing the size, shape and topography of vessel lumens for facilitating implantation of a prosthetic heart valve is known from US2008/0009746 A1. In the known method a catheter based device is used for determining at least one physical parameter of the cardiac valve and surrounding tissue in a body of a patient. For this purpose an assessment member provided near the distal end of a catheter is introduced to a treatment location within the patient, like the native cardiac valve, wherein the assessment member is activated for performing assessment for providing information to a clinician. The assessment member may relate to an intra cardiac echo, 3D ultrasound, electrode-based mapping and imaging device, electronic topographical mapping device. In the known method in addition an external imaging, like MRI or CT may be used.

It is a disadvantage of the known method that assessment of quantitative information pertaining to the target area is obtained invasively and substantially directly during the intervention. As a result, the patient may have to be conditioned for a longer period of time deteriorating workflow of the intervention. In addition, due to the fact that the clinician obtains quantitative information during the intervention there may be no time for optimization or other suitable brain storming.

SUMMARY OF THE INVENTION

It is an object of the invention to provide a method for optimization workflow of a medical intervention particularly in the field of heart valve transplantations and stent placements.

To this end a method according to the invention, comprises the steps of:
reconstruction of an image of a target area representative of an envisaged intervention based on imaging dataset;
automatically selecting an optimal viewing direction for enabling a pre-operative quantitative analysis.

The technical feature of the invention is based on the insight that an a-priori acquired imaging dataset, like CT data, MRI data, 3D ultrasound data, X-ray angio data or the like may be used for determination an optimal viewing direction or directions for enabling quantitative analysis of the target area (i.e. heart valves, vessels, apical region of the heart and the like). It will be appreciated that the imaging dataset may relate to a three-dimensional dataset or a four-dimensional dataset. In the latter case dynamic studies of the target area are enabled.

It will be appreciated that the optimal viewing direction is defined as a direction wherein a diameter of the heart valve may be measured, i.e. a viewing direction substantially perpendicular on a plane of the heart valve. It will be appreciated that due to the fact that for different individuals the heart is oriented differently in the three-dimensional space the optimal viewing direction may only be defined with respect to the heart anatomy.

For the stent placement procedure, the imaging data set may relate to an image of a vessel. The optimal viewing direction in this case is defined as a direction wherein a local dimension of the lumen of the vessel may be determined, i.e. the optimal viewing direction is substantially perpendicular to the lumen of the vessel. It will be appreciated that due to the fact that the vessel is a non-linear structure, the optimal viewing direction may be a dynamic parameter.

In an embodiment of the method according to the invention, wherein the intervention relates to a heart valve replacement, the target area may comprise a heart valve and a portion of a lumen arranged in fluid communication with the heart valve. Alternatively or additionally, the target area may comprise a heart valve and one or more chambers of the heart. Still additionally or alternatively, the target area may comprise the heart valve and the apex of the heart.

In a further embodiment of the method according to the invention, wherein the intervention relates to a heart valve replacement, the method further comprises the steps of:

accessing image data representative of the heart valve and the surrounding anatomy;

based on the image data calculating a pre-determined reference line for reconstructing an optimal image projection comprising the heart valve.

It will be appreciated that the heart valve replacement may relate to replacement of any of the following heart valves: mitral valve, aortic valve, pulmonary valve and tricuspid valve. It is found that quantitative analysis does not necessarily have to be based on planar geometries. In some instances, for example, when dimensions and properties of a vessel or lumen are to be determined visualization along a curved line may be advantageous, especially when such visualization provided a clear view on the vessel cross-section and on a junction between the vessel and the heart. Preferably, for the pre-determined reference line a centre lumen line is selected.

In a further embodiment of the method of the invention the image projection is obliquely oriented with respect to the centre lumen line.

It is found that heart valves are optimally viewed in an oblique projection, wherein one or more two-dimensional images representing the target area may be reconstructed using a per se known technique of a multi-planar reconstruction along the reference line. It is further found that heart valves are surprisingly clearly visible on such oblique projections.

In a further embodiment of the method according to the invention, wherein for the reference line the center line is used, the method further comprises the step of defining a centre line annulus point position using the image projection.

It will be appreciated that this step may be carried out interactively, wherein a clinician provided with the automatically calculated center line of the lumen may reposition the centre line annulus point position and annulus plane orientation, preferably in a combined viewing screen comprising three multi-planar reconstruction images calculated about the center line. It will be appreciated that the annulus point position may be determined automatically. The method used to determine the annulus point is to analyze the planes perpendicular along the center line. In the area where the annulus valve is located, the planes contain calcifications and tissue which can be detected by assessing the diversity in voxel values. The annulus point is then positioned in the middle of the area on the center line.

It is also possible to seed two points defining a plane, for example an annulus plane. The method according to the invention may comprise a step of automatically defining the 90 degrees line perpendicular to this plane that enables an angle measurement to be made with respect to this 90 degrees line. This feature may be advantageous as it allows the user to measure angles orthogonally to the annulus plane for preparing the intervention.

In a still further embodiment of the method according to the invention, it further comprises the step of using the rendered image view for assessing features in the heart valve and/or the vessel associated with the lumen. For example, for the features of the vessel a length of the vessel, and/or a diameter of the lumen may be selected. It is found to be advantageous to select for the rendered image, a MinIP, a MIP, a stretched curved MPR, a volume rendered, or an average IP.

For example, in a suitable graphic user interface a number of optimal or preferential viewing directions may be provided in separate sub-windows, wherein each viewing direction may serve its own purpose. For example, a compass viewing sub-window may be provided for facilitation orientation in 3D. In addition, a minimum intensity projection (MinIP) sub-window may be provided for assessing anatomy of leaflets, like their number and configuration. A maximum intensity projection (MIP) or a volume rendered sub-window may be provided for assessing calcifications on the inner surface of the lumen or on the heart valves. Still additionally, stretched curved MPR views may be provided for enabling length measurements. The stretched curved MPR are reconstructed along the lumen center line, and can be rotated along the lumen center line. Such sub-windows may be toggled with double oblique views for enabling diameter measurements. It will be appreciated that a selection of suitable angulation for the oblique or double oblique imaging lies within an ordinary skill of the person skilled in the art. It will be appreciated that the sub-windows may be provided for facilitating control whereas quantitative analysis may be carried out in a fully automated way, for example based on the MRI or CT pixel values.

For example, a suitable rendered image, as discussed above, may be used for assessing abnormalities in the heart valve and/or the vessel. It will be appreciated that abnormalities may relate to calcifications, aneurism's, stenosis, abrupt change of lumen spatial angulation and so forth.

In a still further embodiment of method according to a further aspect of the invention, the method further comprises the step of using the MIP view for calculating an optimal setting of an imaging device for acquiring an image of the heart valve mimicking the MIP image. It is found that additional advantages with respect to the ease of comprehension of the complex anatomy and improving the workflow are obtained when the images are rendered in circular or in "hockey puck'-like shaped volume of interest. It will be further appreciated that the hockey-puck volume of interest represents a cylindrically shaped geometry. Accordingly, those skilled in the art having knowledge of image rendering in the orthogonal geometry may readily apply the rendering methods for the circular volume of interest or the cylindrical volume of interest (the hockey puck).

It will be appreciated that the method according to the invention is preferably carried-out beforehand, i.e. substantially in advance to the intervention. Accordingly, the clinician may determine an optimal viewing angle for viewing the heart valve interactively or in a fully automated way. It may be preferable to record this angle for installing an imaging device, for example a C-arm of the operation room for reproducing the simulated image in reality. Such control of the imaging device is advantageous not only because it saves considerable time (about 0.5 hour) for on-line optimization of the imaging angle, but contributes to increasing safety of the procedure, as lower amounts of contrast medium have to be introduced into the system of the patient for procedures which are shortened in time.

In a still further embodiment of a method according to a further aspect of the invention the step of calculating a stretched curved MPR view for enabling a length measurement along the center line lumen is envisaged.

It will be appreciated that this step may be carried out for calculating a length of a lumen for either the transluminal heart interventions or angiographic studies. In both cases based on determination of the lumen length a suitable catheter may be selected In a still further embodiment of a method according to an aspect of the invention, it further comprises the step of analyzing a diameter of the lumen in the MPR view.

It is found that the diameter of the lumen may be accurately determined using the MPR view along the centerline of the lumen, wherein for diameter determination any suitable known calculation technique may be used. For example, a virtual coin approach may be used, or other suitable technique, for example based on pixel values.

In a still further embodiment of the method according a further aspect of the invention, the method further comprises the step of providing indications of tortuosity of vessel based on said analysis.

Preferably, tortuosity is calculated along the vessel and is presented as a graph or a color code along the vessel or superposed on it. This feature has an advantage of providing quantitative data to the clinician in a highly perceptive way. In particular, dangerous regions or areas requiring specific attention maybe highlighted by a color or any other suitable indication.

In a further embodiment of the method according to a still further aspect of the invention, the target area comprises a heart valve and an apex of the heart, the method further comprising the step of defining a transapical line of approach.

It is found that by suitably rendering the imaging dataset and by providing an optimal viewing projection, for example corresponding to a minimum distance between the heart valve and the apex the transapical line of approach may be securely defined. Due to this feature safety of the procedure is improved next to improving the workflow as the clinician can make a plan of the future intervention beforehand.

For example, the method of the invention may be adapted to automatically calculate a position of an apical seeding point for establishing the optimal line of approach. In this way the clinician is provided with a first educated guess regarding the point of entry into the heart. Suitably, the graphic user interface allows the clinician to set the second point in the valve and to modify respective positions of these two points iteratively.

It is also possible that the user is enabled to analyze multiple approach routes to the target area and to quantitatively compare the results. The software may allow the user to first analyze the heart valve itself as to whether is it applicable to receive an aortic heart valve implantation and, if so, subsequently the user has the possibility to determine how to best perform the procedure on the patient depending on the patient specific anatomy which is analyzed during the different approach methods (for example, transapical, transfemoral, or transsubclavian approaches).

According to a still further embodiment of the method according to a still further aspect of the invention, the method further comprises the step of determining an entry angle for a catheter based on the selected line of approach.

This feature is advantageous as catheter bending may be simulated for checking whether the selected line of approach is feasible in practice. For example, additional points next to the apex entry point and the annulus point may be defined for calculating catheter bending in real space, as said entry angle may be variable along the line of approach. Preferably, the graphic user interface enables the user to rotate the rendered view with respect to the catheter for enabling a better comprehension of the underlying anatomy by the user.

In a still further embodiment of a method according to a still further aspect of the invention, the intervention relates to a stent placement, wherein the target area relates to a region of a vessel comprising an aneurism or a stenosis.

A method according the invention may further comprise the step of using the rendered image for calculating an optimal setting of an imaging device for acquiring an image of the aneurism or stenosis mimicking the rendered image. Preferably, for the rendered image, a MinIP, a MIP, a stretched curved MPR, a volume rendered, or an average IP is selected.

In a further embodiment of the method according to the invention the method further comprises the step of providing indications of tortuosity of vessel wherein aneurism or the stenosis is detected.

Preferably, in a still further embodiment of the method according to the invention, it further comprises the step of providing indications on calcification along the lumen of the vessel wherein the aneurism or stenosis is detected.

It will be appreciated that image reconstruction and generation of suitable optimal projections, like stretched curved MPR's with respect to a center line of the lumen may be carried out along the lines as is explained in the foregoing. In particular, MIP's and MPR's may be rendered for enabling determination of the length of the vessel, dimensions of the abnormality (aneurism or stenosis). As a result, performing of quantitative analysis of the vessel anatomy, like suitable geometric parameters may be enabled.

In a still further embodiment of a method according to a still further aspect of the invention, the method further comprises the step of updating a pre-defined stent template form based on results of the quantitative analysis.

It will be appreciated that quantitative data generated during analysis of the vessel geometry, in particular running diameter and a total length along the lumen center line, may be automatically provided in a suitable stent form template, which may be used for documentation and reporting purposes. In this way a chance of a human error for selecting a suitable stent may be reduced. An exemplary embodiment of the stent form template is discussed with reference to FIG. 6.

A computer program according to an aspect of the invention comprises instructions for causing a processor to carry out the steps of the method according to any one of the preceding claims.

A graphic user interface according to an aspect of the invention comprises a plurality of graphic windows for visualizing steps of the method as is discussed with reference to the foregoing. Exemplary embodiments of the graphic user interface will be discussed in more details with reference to the Figures.

A system of optimizing workflow for an intervention according to an aspect of the invention, comprises a processor arranged for:
  reconstruction of an image of a target area representative to an envisaged intervention based on imaging dataset;
  automatically selecting an optimal viewing direction for enabling a pre-operative quantitative analysis.

Preferably, the system further comprises a display unit for feed-backing results of image reconstruction and analysis. It will be appreciated that the display unit may be remotely arranged with respect to the processor. In addition, it will be appreciated that a plurality of display units may be provided, for example for purposes of remote patient discussions or tele-conferencing. It will be appreciated that a system according to the invention may comprise a personal computer, a laptop, or it may be based on a graphic workstation.

In an embodiment of the system according to a still further aspect of the invention, the system comprises a device arranged to receive instructions from the processor based on results of the pre-operative quantitative analysis for carrying-out the intervention. For example, an imaging device or a suitable automatic manipulator conceived to carry out at least a portion of the intervention are contemplated.

It is found that by providing an integrated system comprising a data analysis component and a patient handling component a substantially unique closed system may be provided which still further may improve the workflow of medical interventions and may reduce errors due to the human factor.

Preferably, according to a further aspect of the invention, the system further comprises an imaging unit arranged to receive instructions from the processor for enabling imaging during the intervention.

It is found that when the imaging unit, like a C-arm is operationally coupled to the system according to the invention the workflow of medical interventions may be improved still further and errors due to the human factor may be still further reduced.

These and other aspects of the invention will be discussed in more detail with reference to the Figures, wherein like reference signs represent like features. It will be appreciated that the Figures are provided for illustration purposes only and may not be used for limiting the scope of appended claims.

DETAILED DESCRIPTION OF THE PREFERRED EMBODIMENTS

Figure 1:
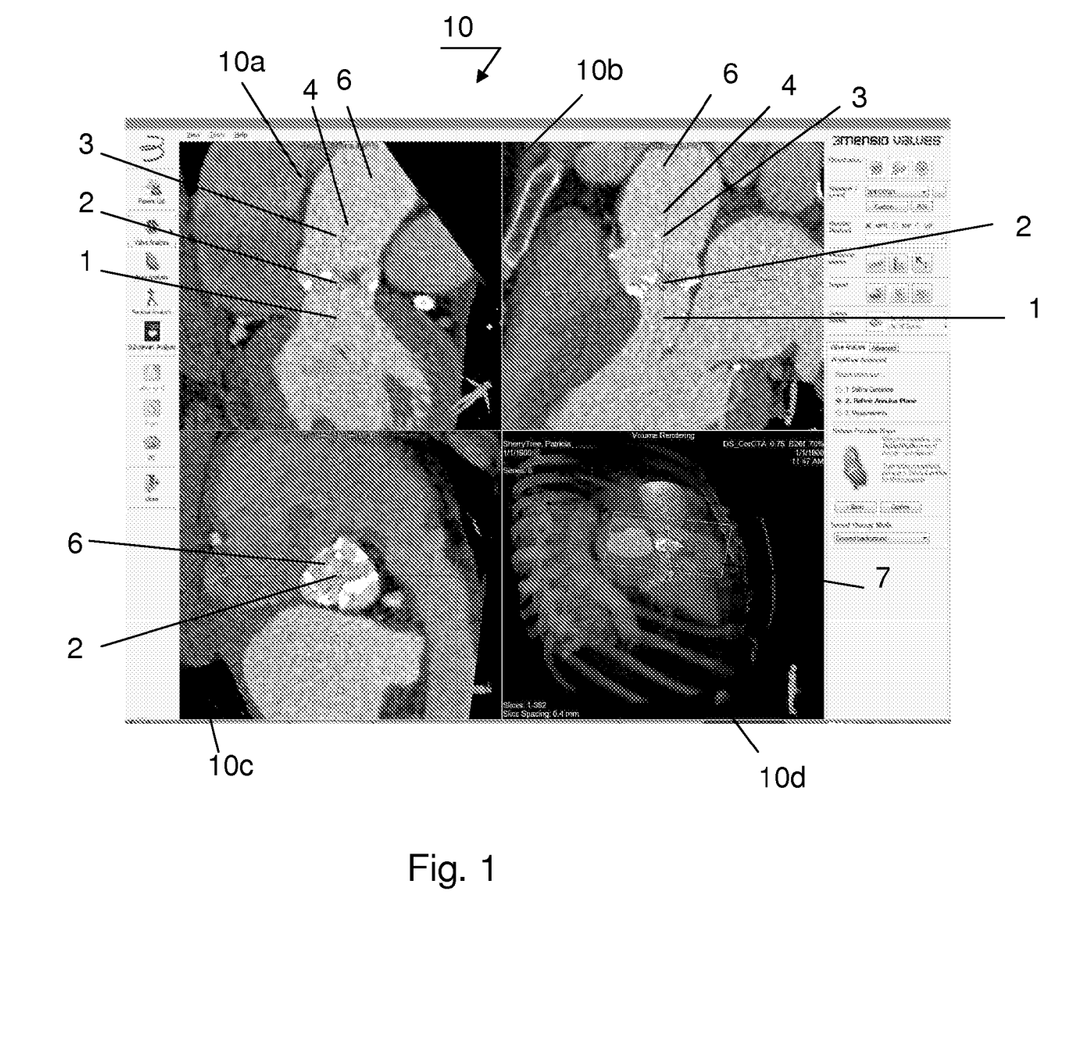
FIG. 1 presents an embodiment of a graphical user interface according to a first aspect of the invention.

FIG. 1 presents an embodiment of a graphical user interface according to a first aspect of the invention. In the present embodiment of a graphic user interface 10 four sub-windows 10a, 10b, 10c and 10d are provided. It will be appreciated that a number of suitable rendered optimal projections may be customized tailoring demands of a particular situation.

Sub-window 10a presents a reconstructed image of a plane of aortic valve of a human heart, wherein a centerline of the lumen (aorta) is given by reference number 4. Along the curved center line 4 a number of reference points may be provided in an automatic, semi-automatic or manual way.

For example, points 1 and 3 may correspond to begin and end of a relevant trajectory along the vessel 6 (aorta). The point 2 corresponds to the annulus point position, which may be determined automatically during image reconstruction and analysis, or, it may be determined semi-automatically or manually. It will be appreciated that it may be possible to readjust a position of the annulus point position after it is seeded in an automatic way. Besides the annulus position, the annulus plane orientation may be also determined automatically or manually.

Due to the fact that for optimal imaging of heart valves reconstruction of oblique images may be required, the sub-window 10a may comprise an orientation indicator animated in a suitable way.

Sub-windows 10b, 10c present a second oblique image and a further oblique image, respectively, which may be rendered together with the image in sub-window in 10a using an MPR reconstruction.

Window 10d may be used for presenting 3D reconstruction of anatomy in the imaging dataset, wherein the current plane shown in projection 10a, 10b, 10c may be indicated by a frame 7.

Accordingly, due to the fact that the heart valve 6 shown in the sub-window 10c is depicted in the optimal projection, accurate analysis of the heart valve parameters and features, such as leaflets is enabled. In addition, due to the fact that the graphic user interface 10 may be used as a tool for planning a medical intervention (in this case—replacement of a heart valve) the workflow may be improved as the clinician has a clear and easy understanding of the otherwise complicated geometry.

It will be appreciated that the graphic user interface 10 may comprise a number of supplementary regions, which may be used for input/output operations with respect to data or commands as well as for feedbacking patient ID data. Preferably, the graphic user interface is used for accessing hospital information system (HIS) or any other suitable database for selecting patient data. It will be appreciated that in the context of the present application the image data may refer to raw image data, or to processed image data. For example, initial analysis of the image data may be carried out automatically as a batch job beforehand.

The graphic user interface 10 may comprise a number of modules, like Valve Analysis, Apex Analysis, Femoral Analysis, Subclavian Analysis or the like, which may be used in an alternative fashion if the context of the casus allows it. It may be advantageous to subject the same patient imaging dataset for analysis for different intervention approaches, like a transapical approach or transfemoral approach for deducing an optimal strategy for the medical intervention. Due to this feature the workflow is further improved and the accuracy of the intervention (heart valve replacement or stent placement) may be improved.

The graphic user interface 10 may further comprise suitable tools for enabling distance measurements, angle measurement or measurements of other type, which may be carried out automatically or in a manual mode.

Figure 2:
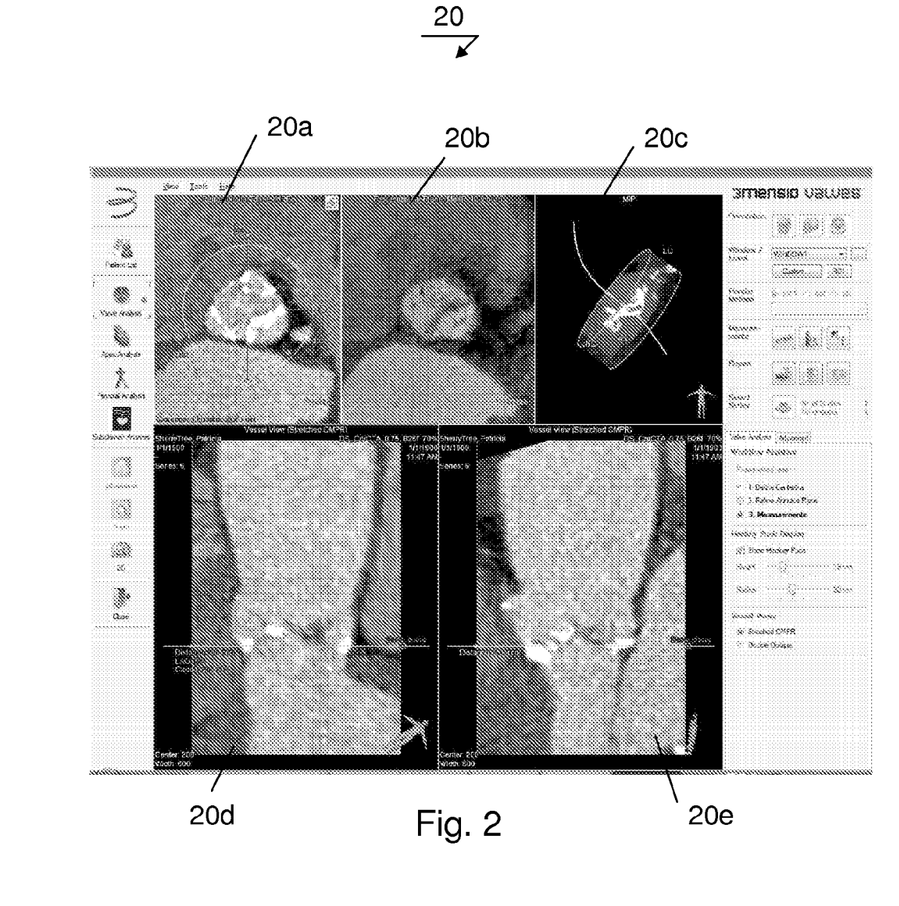
FIG. 2 presents an embodiment of a graphical user interface according to a second aspect of the invention.

FIG. 2 presents an embodiment of a graphical user interface according to a second aspect of the invention. In the present embodiment a Valve Analysis screen is presented, which may be used for obtaining quantitative information about the vessel and its spatial position.

For example, the Valve Analysis screen 20 may comprise a suitable plurality of sub-windows, for example sub-windows 20a, 20b, 20c, 20d, 20e. The sub-window 20a may be used as a compass viewer for assisting the user in orientation of two sub-windows 20d, 20e. The sub-window 20b may relate to a MinIP view for assessing valve anatomy, for example relating to number and condition of the leaflets. The sub-window 20c may be used for visualizing results of the MIP or volume rendered image about the lumen center line. This view is particularly useful for assessing calcifications as well as for establishing an optimal imaging angle of a C-arm. The sub-windows 20d, 20e relate to stretched curved MPR views enabling quantitative determination of the lumen length along the lumen center line.

Preferably, the sub-windows 20d, 20e may be toggled between the MPR view and the double oblique view, the latter enabling diameter measurement of the lumen.

It will be appreciated that the view 20a may relate to the optimal viewing direction according to the invention.

The image presented in view 20c may be referred to as a hockey puck view. The hockey puck view is a cylindrical area with a configurable diameter and a configurable height. The view is used to focus the user on the heart valve itself by removing any surrounding voxels that are outside the hockey puck confines that may obstruct a clear view of the heart valve.

Different render methods (MIP/MinIP/Volume Rendering) may be used to show calcifications of the heart valve, the dynamics of the heart valve itself using 4D data, as well as the anatomy of the heart valve.

It will be appreciated that data rendering may be carried out either starting from a 3D imaging data set or a 4D imaging dataset, the latter allowing for a dynamic study as a function of time. For example, dynamics in leaflets behavior as a function of heartbeat and the phase therein may be studied.

Figure 3:
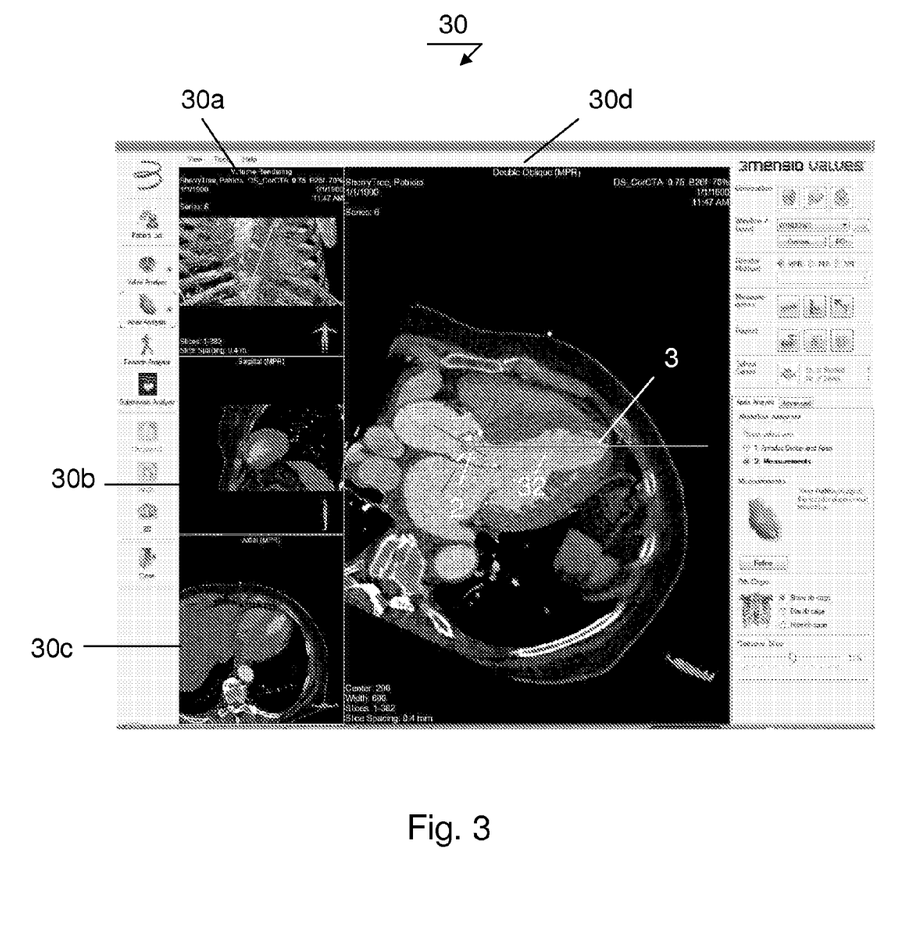
FIG. 3 presents an embodiment of a graphical user interface according to a third aspect of the invention.

FIG. 3 presents an embodiment of a graphical user interface according to a third aspect of the invention. In this exemplary embodiment an Apex Analysis screen 30 is presented. In this case, for example, the sub-windows may relate to sub-windows 30a, 30b, 30c depicting regular orthogonal reconstruction slices and a relatively larger sub-window 30d presenting an oblique slice through the heart, which runs through the annulus point 2. This projection is particularly useful, as an optimum line of approach for transapical interventions may be determined. It will be appreciated that the method according to the invention enables the user to study a suitable plurality of line of approaches and to compare them quantitatively for making an educated selection of a preferred intervention route. Suitable reporting may be envisaged as well, like a length on the route, or other clinically relevant parameters, like angles, vicinity to critical organs or regions and the like.

The optimal line of approach 32 may run between the annular point 2 and the apex point 3. Preferably, the graphic user interface supports a real-time changing of point positions for analysis and optimization. It is also possible that some regions are organs are virtually dimmed out or otherwise highlighted or de-highlighted for enabling an easy comprehension of the anatomy and the planned intervention by the clinician.

It may be also possible to suitably rotate around line of MPR view for path analysis, for example a virtual catheter size viewing may be envisaged, wherein thickness of the catheter may be adapted.

In addition the sub-window 30d may be used for analyzing the entry angle for the catheter. The entry angle may be of a crucial importance, for example for checking whether induced catheter bending do not supersede allowable tolerances. In order to work around corners or the like, it may be possible to define additional points between the point 2, 3.

In addition, the sub-window 30d may be used for enabling measurement of lengths of myocardium and septal wall thickness for planning the intervention.

Accordingly, due to one or more above features workflow of the heart valve replacement intervention may be substantially optimized, wherein probability of a human error may be reduced.

Figure 4:
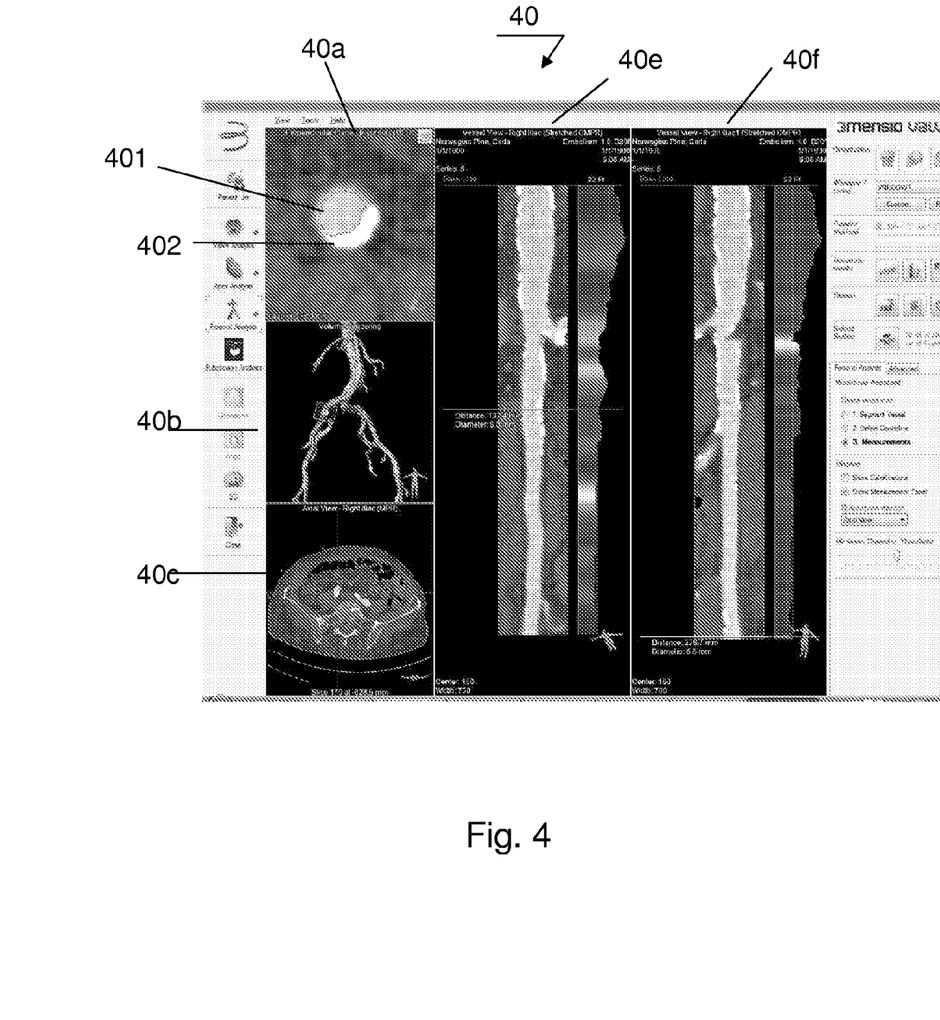
FIG. 4 presents an embodiment of a graphical user interface according to a fourth aspect of the invention.

FIG. 4 presents an embodiment of a graphical user interface according to a fourth aspect of the invention. In this exemplary embodiment a Femoral Analysis screen 40 is discussed. The screen 40 may also comprise a suitable plurality of windows, some of which may be used for reference, like windows 40a, 40b, 40c. A central portion of the screen 40 may be used for the sub-windows 40e, 40f for depicting suitable vessels, in casu, left and right stretched curved MPR views.

Advantageously quantitative supplementary information is provided in sub-windows 40e, 40f. For example, graphs representing a running value of a lumen diameter, wherein, advantageously regions of particular attention, like narrowings may be highlighted. For example, a critical value of 23 F (about 8 mm) may be indicated throughout the graph for immediate perception whether a particular catheter fits into the lumen. The sub-window 40a, depicting a running lumen diameter may be synchronized with the area along the window 40d, 40e so that when a cursor falls within the image of 40e a cross-sectional image of the lumen 402 together with a fitted coin 401 corresponding to the same 'longitudinal' level may be shown. In this way the user may easily check whether the automated algorithm did not fail while calculating a running value of the lumen diameter.

In addition, regions having particular properties, like tortuosity data, may be suitably indicated along the graph. It will be appreciated that such indication may be carried out using color-code or by implementing other illustrative means.

It will be appreciated that the view 40a may relate to the optimal viewing direction according to the insights of the invention.

Figure 5:
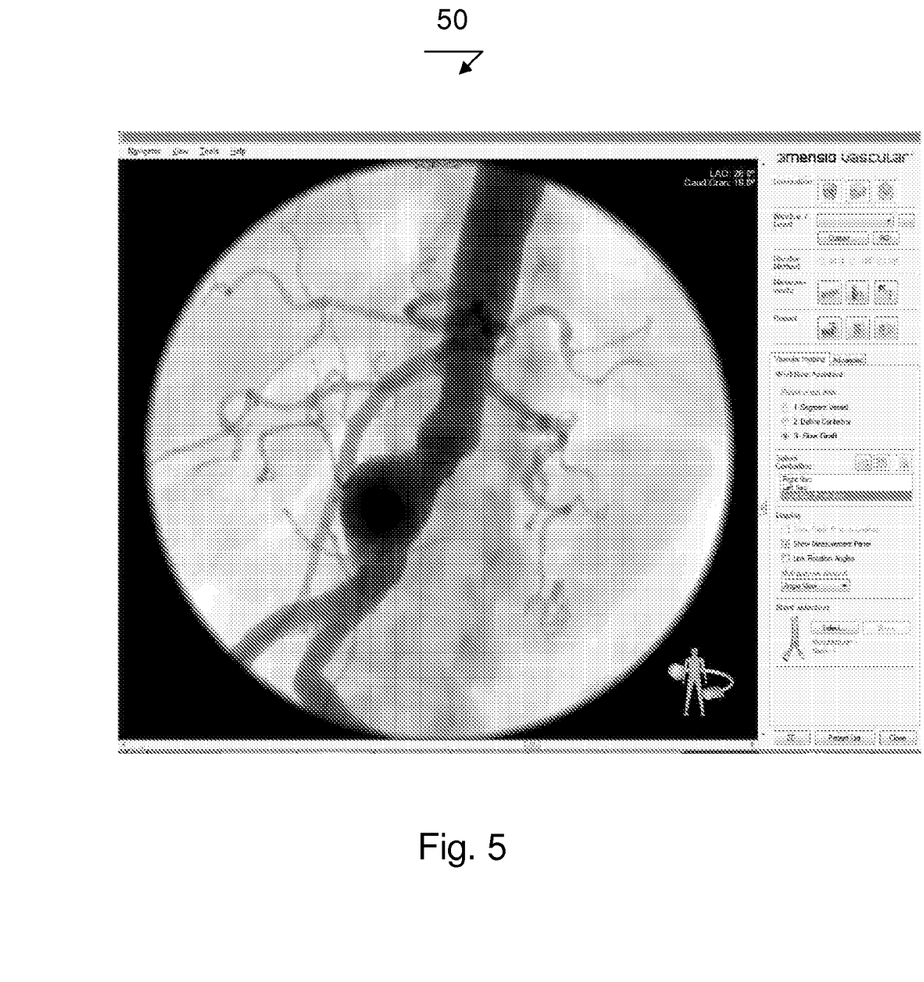
FIG. 5 presents an embodiment of a graphical user interface according to a fifth aspect of the invention.

FIG. 5 presents an embodiment of a graphical user interface according to a fifth aspect of the invention. In the present exemplary embodiment an Angiographic View screen 50 is presented, which may be a separate data analysis package, or, it may be a part of the data analysis package discussed with reference to FIG. 1. Image 50 shows reconstructed data enabling interactive viewing and analysis of position angles for the C-arm for optimal viewing of patient anatomy during intervention.

Also in this case it is preferable that panning, zooming and windowing of this view is rendered along the center line of the lumen. The segmented vessels may be highlighted using per se known thresholding methods. When the optimal projection is established automatically or interactively, the corresponding position of the C-arm for generating such image may be recorded.

As a result, workflow in the operation room is improved. In case when the C-arm is controllable (directly or indirectly) by the processor operating the graphic user interface, the position of the C-arm may be automatically installed upon uploading saved data. It will be appreciated that the functionality discussed with reference to angiography may also be applied for analyzing valve leaflets, as it may be important to understand the structure and the spatial position of the leaflets prior to replacing the heart valve.

In addition, it is possible that vessel anatomy is studied in more detail using a graphics tool. For example, a clock position overlay may be used to determine the angle in which a vessel branches off another vessel. In particular such tool may be used to determine the angles under which the renal arteries branch off the aorta. The angle is measured either in degrees or the position on the clock where 12 o'clock is defined as pointing towards the posterior side of the patient and looked at from above. For fenestrated stents theses angles provide valuable information for guiding the intervention.

Figure 6:
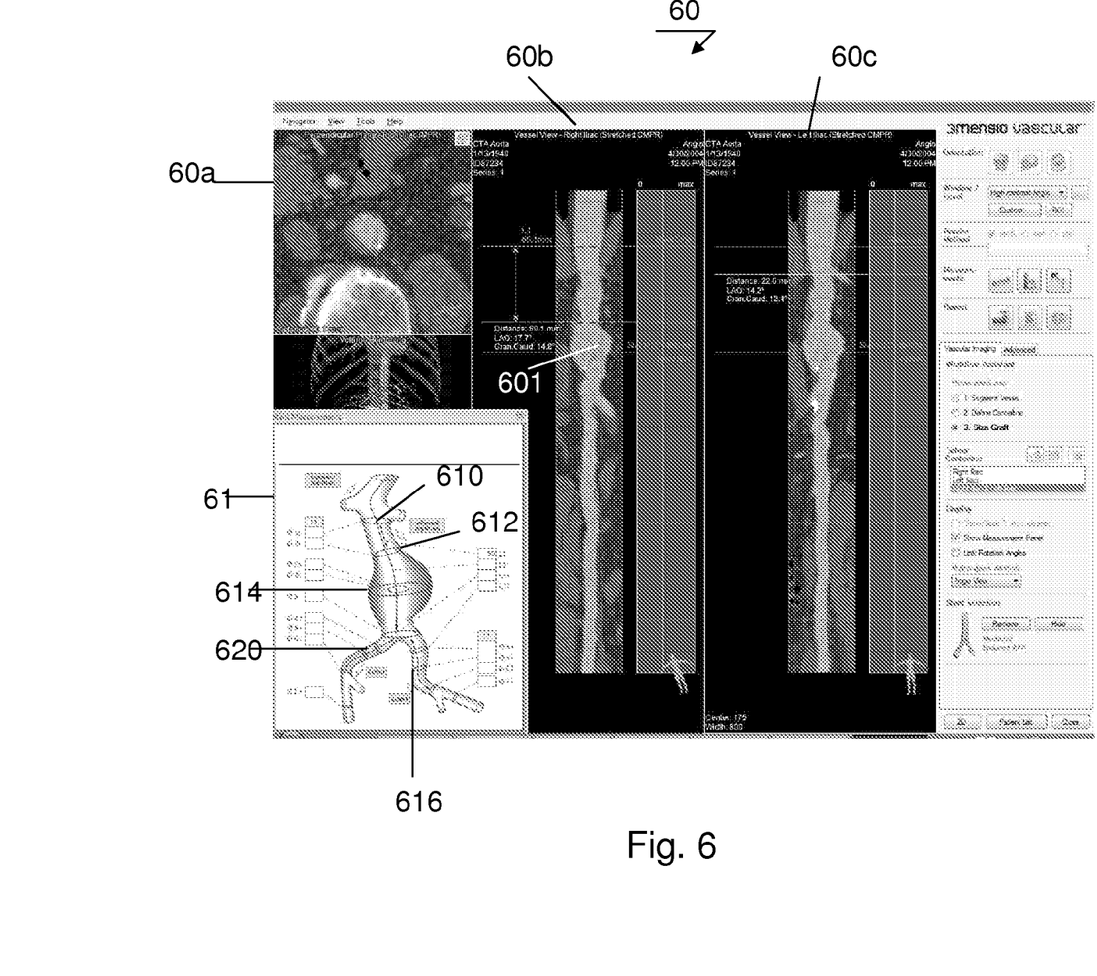
FIG. 6 presents an embodiment of a graphical user interface according to a sixth aspect of the invention.

FIG. 6 presents an embodiment of a graphical user interface according to a sixth aspect of the invention. In this exemplary embodiment a Stent Form Templates screen 60 is presented. The screen 60 may comprise a number of sub-windows, like a transversal view, a first longitudinal view 60b (right iliac) and a second longitudinal view 60c (left iliac). In accordance with aspects of the invention discussed earlier, the windows 60b, 60c may relate to a stretched curved MPR views. Preferably, the views 60b, 60c are linked with an automatic measuring tool, for determining a running value of the lumen diameter of the vessels under consideration.

Preferably, results of the automatic measurement of the lumen diameter are automatically recorded in a Stent Form Template, comprising a number of assigned characteristic areas 610, 612, 614, 620, 616 for enabling an educated selection of a suitable stent for treating the aneurism 601. It will be appreciated that due to the automatic data log the workflow may further be improved and human errors may be avoided.

It will be further appreciated that a similar template may be used to enabling the user to analyze multiple implant devices and to quantitatively compare the results. For example, for the heart valve replacement module the software may be adapted to add form templates that can be tied to the different measurements carried out on the rendered image It will be appreciated that while specific embodiments of the invention have been described above, that the invention may be practiced otherwise than as described. In addition, isolated features discussed with reference to different figures may be combined.

The invention claimed is:

1. A method of optimizing workflow for an intervention relating to a heart valve replacement, comprising:
    reconstruction of an image of a target area representative of the intervention based on an imaging dataset, wherein the target area comprises a heart valve and a portion of a lumen arranged in fluid communication with the heart valve;
    automatically selecting an optimal viewing direction for enabling a pre-operative quantitative analysis of features of the intervention; and
    using the image of the target area to calculate a reference line that is used to automatically derive an optimal image projection of the target area.
2. A method according to claim 1, wherein:
    a center lumen line is selected for the reference line.
3. A method according to claim 2, wherein:
    the optimal image projection is obliquely oriented with respect to the center lumen line.
4. A method according to claim 3, further comprising:
    defining a center line annulus point position using the optimal image projection.
5. A method according to claim 4, further comprising:
    reconstructing a rendered image along the center lumen line.
6. A method according to claim 5, further comprising:
    using the rendered image view for assessing features in the heart valve and/or the vessel corresponding to the lumen.
7. A method according to claim 6, wherein:
    for the features of the vessel a length of the vessel, and/or a diameter of the lumen are selected.
8. A method according to claim 6, further comprising:
    using the rendered image for calculating an optimal setting of an imaging device for acquiring an image of the heart valve mimicking the rendered image.
9. A method according to claim 5, wherein:
    a rendering method for generating the rendered image is selected from a group of rendering methods, the group of rendering methods consisting of a MiniP method, a MIP method, a stretched curved MPR method, a volume rendered method, and an average IP method.
10. A method according to claim 9, further comprising: providing indications of tortuosity of vessel.
11. A method according to claim 9, further comprising: providing indications on calcification along the lumen.
12. A method according to claim 1, wherein:
    the target area further comprises an apex of the heart, and the method further comprises defining a transapicalline of approach.
13. A method according to claim 12, wherein:
    an initial seed for position of the apex of the heart is placed automatically.
14. A method according to claim 13, further comprising:
    determining an entry angle for a catheter based on the transapicalline of approach.
15. A method according to claim 14, wherein:
    said entry angle is variable along the transapicalline of approach.
16. A method according to claim 1, wherein:
    the imaging dataset corresponds to a three-dimensional or a four-dimensional dataset.
17. A non-transistory computer program comprising instructions for causing a processor to carry out the method of claim 1.
18. A method of optimizing workflow for an intervention relating to a stent placement, comprising:
    reconstruction of an image of a target area representative of the intervention based on an imaging dataset, wherein the target area comprises a region of a vessel that includes an aneurism or a stenosis; and
    automatically selecting an optimal viewing direction for enabling a pre-operative quantitative analysis of intervention features of the intervention;
    determining a center line of the lume of the vessel;
    reconstructing a MPR view along the center line of the lumen of the vessel; and
    performing quantitative analysis of the anatomy of the vessel.
19. A method according to claim 18, further comprising:
    automatically updating a pre-defined stent template form based on results of the quantitative analysis, and wherein said vessel anatomy comprises lumen diameter.
20. A method according to claim 18, wherein:
    the imaging dataset corresponds to a three-dimensional or a four-dimensional dataset.
21. A non-transitory computer program comprising instructions for causing a processor to carry out the method of claim 18.
22. A system of optimizing workflow for an intervention relating to a heart valve replacement, comprising a processor arranged for:
    reconstruction of an image of a target area representative to an envisaged intervention based on an imaging dataset, wherein the target area comprises a heart valve and a portion of a lumen arranged in fluid communication with the heart valve;
    automatically selecting an optimal viewing direction for enabling a pre-operative quantitative analysis of features of the intervention; and
    using the image of the target area to calculate a reference line that is used to automatically derive an optimal image projection of the target area.
23. A system according to claim 22, further comprising:
    a device arranged to receive instructions from the processor based on results of the pre-operative quantitative analysis for carrying out at least a part of the intervention.

* * * * *